United States Patent [19]
Miura et al.

[11] 4,356,173
[45] Oct. 26, 1982

[54] IGM DERIVATIVES AND PROCESS FOR THE PREPARATION THEREOF

[75] Inventors: Shuzi Miura, Hino; Tsunemasa Yoshida, Hachioji; Shoji Ono, Kodaira; Yasuhiko Masuho; Shuzo Sawada, both of Hino, all of Japan

[73] Assignee: Teijin Limited, Osaka, Japan

[21] Appl. No.: 255,087

[22] Filed: Apr. 17, 1981

[30] Foreign Application Priority Data

Apr. 18, 1980 [JP] Japan .................................. 55-50259

[51] Int. Cl.³ .................... A61K 35/14; A61K 37/00; C07G 7/00
[52] U.S. Cl. .................................. 424/101; 424/177; 260/112 R
[58] Field of Search .......................... 424/177, 101; 260/112 R

[56] References Cited
PUBLICATIONS

A. M. Egorov et al., Chem. Abstr. 76, (1972) 70873e.

*Primary Examiner*—Delbert R. Phillips
*Attorney, Agent, or Firm*—Sughrue, Mion, Zinn, Macpeak & Seas

[57] ABSTRACT

IgM derivatives into which acyl groups expressed by the following formula (I) are introduced to make their anticomplement activity weak by acylating the free amino groups existing in IgM up to 1–90% (acylation percentage)

$$-COR \qquad (I)$$

where R indicates an alkyl group having 1 to 4 carbon atoms, or a carboxylated alkyl group expressed by $-(CH_2)_mCOOH$ (m is 2 or 3) or $-CH=CHCOOH$.

These IgM derivatives can be used for making immunoglobulin preparations for intravenous injection use.

10 Claims, 1 Drawing Figure

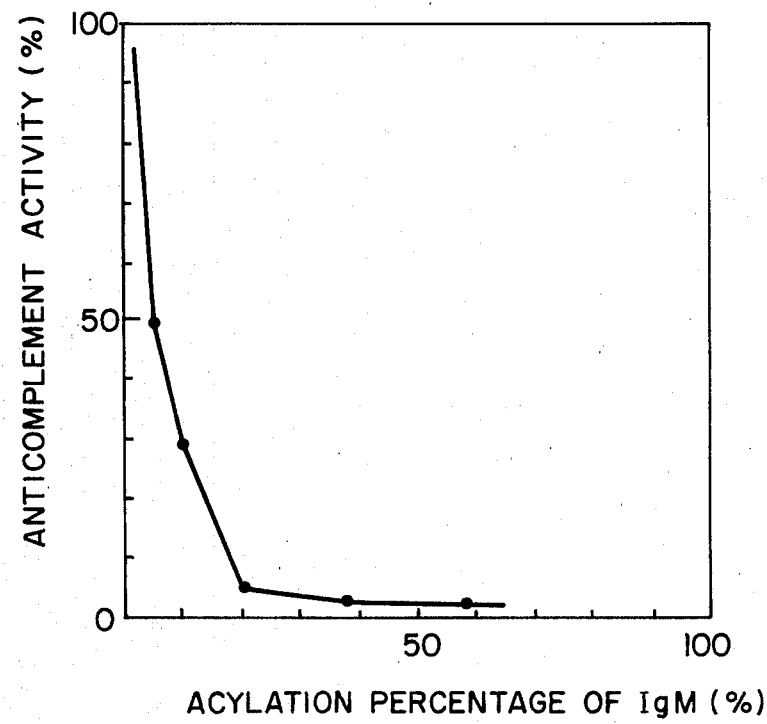

IGM DERIVATIVES AND PROCESS FOR THE PREPARATION THEREOF

BACKGROUND OF THE INVENTION

1. Field of the Invention

The present invention relates to IgM derivatives, which are obtained by the treatment of an acylating agent to immunoglobulin M (IgM) whereby free amino groups existing in IgM are partially acylated, and a process for the preparation thereof. More particularly, the present invention relates to IgM derivatives acylated to have their inherent antibody activity maintained undamaged while their anticomplement activity is weakened, thus being made usable for intravenous injection.

2. Description of the Prior Art

It is generally known that, of all human immunoglobulins (Ig), especially IgG is widely used for preventing and treating a special variety of diseases to show marked effects in both prophylactic and therapeutic practices. Incidentally, the biological activities of immunoglobulins differ from each other depending upon their kinds and IgM has the following specific characteristics:

(i) IgM is produced prior to IgG under the stimulus of the antigen to the living body.

(ii) In terms of molecular structure, IgM is a pentamer made of five subunits like the Y-shaped structure described for IgG, having a high binding constant of 10 (IgG has a bivalent) to bind with antigen and no exhibits a strong agglutinating activity against bacteria, especially against Gram-negative bacteria.

(iii) IgM is superior to IgG in both bacteriolytic activity opsonic activity.

It is therefore said that IgM may be more suited as a remedy for bacterial infections diseases than IgG judging from the abovementioned specific characteristics. Based on such a concept, IgM (rich) preparations have naturally attracted medical attention and their research and development have been carried on. Some of IgM preparations for intramuscular injection have already been used to display an assured remedial effect. However, in the case of an intramuscular administration, immediate effects of IgM preparations are hardly expected since they can not be administered in a large dosage to increase the concentration of IgM in the blood quickly. Furthermore, IgM preparations have some problems still remaining unsolved such as a pain caused at the region of injection, delayed absorption, damages caused to IgM due to enzymolysis taking place in the muscular tissue, etc.

Besides, it is concerned about the fact that intravenous injection of IgM, when practiced without being subjected to any pretreatment, will cause a side effect similar to anaphylaxis, which is seen in the case of the intravenous administration of IgG, due to acute activation of the complement prompted by the aggregate which is formed unavoidably in IgM preparations in course of their making. As for the method to mitigate such side effect, several methods are known as a useful mode for IgG to suppress its similar side effect or to lower its anticomplement activity, including an enzyme treatment, S-alkylation treatment, sulfonation treatment, etc. However, these methods raise a problem to remarkably lower the activity proper to IgM by damaging its pentameric molecular structure which is regarded as a source of its strong agglutinating activity.

Because of this problematic molecular structure, the research of IgM preparations for intravenous injection use has been a difficult tack and no successful development has yet been made in spite of such assured merits of intravenous administration of immunoglobulins as proved by the successfully developed IgG preparations which can be safely administered intravenously to widen the scope of medical applications and enhance the efficacy of immunoglobulin in medical treatment.

SUMMARY OF THE INVENTION

After an intensive medical research directed toward the development of IgM preparations which can be safely used for intravenous administration, the present inventors have come to find that, when the free amino groups of IgM are partially acylated by allowing IgM to react with an acylating agent in water, IgM derivatives are obtained with their various antibody activities proper to IgM scarcely damaged while the anticomplement activity of IgM decreases as the acylation of said amino groups proceeds, and have completed the present invention.

More particularly, the present invention is to provide IgM derivatives into which acyl groups expressed by the following formula (I) are introduced to make their anticomplement activity weak by acylating the free amino groups existing in IgM up to 1–90% (acylation percentage)

$$-COR \qquad (I)$$

where R indicates an alkyl group having 1 to 4 carbon atoms, or a carboxylated alkyl group expressed by —(CH$_2$)mCOOH (m is 2 or 3) or —CH=CHCOOH.

BRIEF DESCRIPTION OF THE DRAWING

FIGURE is a drawing to show the relationship between the acylation percentage and the anticomplement activity of a 1% solution of IgM derivative in the case where R is a methyl group in the IgM derivative of the present invention.

DESCRIPTION OF THE PREFERRED EMBODIMENTS

In the present invention, IgM derivatives are obtained by partially acylating the free amino groups arising from amino acid which constitutes polypeptide chains of IgM molecule.

Acylating agents to be used in the present invention are those which can form an acyl group (COR) as defined by the formula (I) upon reacting with free amino groups. To offer examples of such acylating agents, there are carboxylic acids respectively comprising acetic acid (R=CH$_3$ in the formula (I)), propionic acid (R=C$_2$H$_5$), butyric acid (R=C$_3$H$_7$), valeric acid (R=C$_4$H$_9$), succinic acid (R=(CH$_2$)$_2$.COOH), glutaric acid (R=(CH$_2$)$_3$.COOH) and maleic acid (R=CH=CHCOOH), or their unhydrides, or their acid chlorides, or their esters. Heterocyclic acylating agents such as N-acetylimidazole and 3-acetoxy-1-acetyl-5-methylpyrazole can also be used. Especially preferable acylating agents are such acetylating agents as acetic anhydride and acetyl chloride which can introduce acetyl groups (R=CH$_3$) into IgM molecules.

Acylating percentage referred to in the present invention is defined as follows. A mixture prepared by adding 2.0 ml of 0.15 M KBO$_3$ buffer, 0.5 ml of 0.01 M Na$_2$SO$_3$ and 0.5 ml of 0.10% trinitrobenzenesulfonic acid to 0.5 ml of 3% IgM derivative solution is allowed to react at 37° C. for 1 hour. The specific absorbance of trinitrobenzenesulfonic acid reacted with the free amino groups is determined at 420 nm, and the obtained value of absorbance is regarded as the absorbance (A) which corresponds to the total number of the free amino groups existing in IgM. Another absorbance (B) is obtained corresponding to the number of unacylated amino groups, or free amino groups which have reacted with trinitrobenzenesulfonic acid in the reaction of the acylated IgM derivative with trinitrobenzenesulfonic acid conducted under the same conditions as mentioned above. Now the acylation percentage is defined as acylation percentage=(A−B/A)×100(%)

In the present invention, the acylation percentage should be 1 to 90%, preferably 1 to 30%. When the acylation percentage is less than 1%, the anticomplement activity of IgM derivatives is not reduced sufficiently, and when it is more than 90%, acylated IgM is likely to exert a new antigenicity on a living body, which cases are both undesirable in the present invention.

The measurement of anticomplement activity in the present invention is conducted according to the method proposed by Kabat and Mayer (Experimental Immunochemistry, p 225 (1961)). IgM derivatives, whose 1% solution has 50% or lower anticomplement activity, are especially suitable for preparing intravenous injections.

IgM to be used in the present invention is obtained from Fraction-III (F-III) prepared by fractionating, for instance, human blood plasma according to Cohn's method of ethanol fractionation. Acylated IgM derivatives of the present invention may be prepared by acylating thus obtained F-III or by acylating the refined F-III having the increased content of IgM.

In the present invention, the reaction between IgM and the aforementioned acylating agent is conducted in water; however, the presence of an organic solvent in the reaction system is permissible so far as its content is not obstructive to the reaction. The quantitative ratio of acylating agent to IgM varies depending upon the desired acylation percentage; however, it is preferable to use an acylating agent in the range of about 0.5 to 20% based on the weight of IgM. It is proper to keep the pH of the reaction solution in the range of 6 to 10; however, in a case where an anhydride of carboxylic acid is used as an acylating agent, it is desirable to adjust the pH to the mild alkaline range of 7.5 to 8.5. The reaction temperature is usually kept at 50° C. or lower, but a temperature of 0° to 5° C. is suited for the reaction to secure the stability of IgM in the reaction solution and uniformity of the reaction itself, and it is desirable to conduct the reaction with enough stirring to a degree not to cause the denaturation of globulin. It is proper to set the reaction time in the range of 5 minutes to 5 hours. After the reaction is completed, the IgM derivative of the present invention is obtained by successively dialyzing the reaction mixture against water and then a suitable buffer, for instance, normal saline solution of pH 7.4 containing 0.2% polyethylene glycol.

The relationship between the acylation percentage and the anticomplement activity of 1% solution of IgM derivative when R is a methyl group in the IgM derivative of the present invention is shown in FIGURE. It is clearly understood from FIGURE that as the acylation percentage increases, the anticomplement activity decreases sharply. When the acylation percentage is 5%, the anticomplement activity decreases below 50% and when the acylation percentage is higher than 30%, the anticomplement activity decreases remarkably.

An explanation will be offered below on the pharmacological activity, acute toxicity, etc. of the IgM derivatives of the present invention.

(1) Comparison of antibody values between IgM derivative and intact IgM.

Table 1 shows the antibody values of IgM derivative (acylation percentage: 10%), in which R is a methyl group, obtained with typical bacterial strains of coliform bacillus, staphylococcus and bacillus pyocyaneus as compared with the respective antibody values of intact IgM. It can be understood from Table 1 that the antibody values, or the degree of antibody activity proper to intact IgM, are maintained in the IgM derivative of the present invention.

TABLE 1

| Kind of bacterial strain | Antibody value of IgM derivative* | Antibody value of intact IgM* |
|---|---|---|
| Coliform bacillus (E. coli) NIHJ JC-2 | 7.0 | 7.0 |
| Staphylococcus (Staphylococcus aureus) 209P | 6.0 | 6.0 |
| Bacillus pyocyaneus (Pseudomonas aeruginosa) IFO 3080 | 3.5 | 3.5 |

*Logarithm of 47 mg/ml to the base 2.

(2) Comparison of antibody values between IgM and IgG.

The antibody values of IgM (IgM content: 80% or more) and IgG (IgG content: 80% or more), both prepared from the same material (human blood plasma), were determined with the use of clinically isolated bacterial strains. The test was conducted on IgM and IgG both having the concentration of 2%. The obtained result is shown in Table 2.

TABLE 2

| Bacterium | Number of strains | Antibody value of IgM based on antibody value of IgG set at 1 |
|---|---|---|
| E. coli | 9 strains | $2^3-2^5$ |
| Citrobacter | 4 | $2^4$ |
| Ps. aeruginosa | 9 | $2^4-2^5$ |
| Acinetobacter | 3 | $2^1-2^2$ |
| Ser. marcescens | 10 | $2^4-2^5$ |
| E. cloacae | 4 | $2^3-2^6$ |
| Proteus morganii | 10 | $2^4$ |
| E. aerogenes | 3 | $2^2-2^4$ |
| Proteus inconstans | 3 | $2^4$ |

In the above table, IgM shows remarkably high values of antibody activity against all the gram-negative bacteria investigated. This fact gives assurance that IgM, i.e. IgM derivative of the present invention, has a remarkable success in the treatment of bacterial, especially gram-negative bacterial infections.

(3) Value of anticomplement activity of IgM derivatives after lyophilization

Solutions of IgM derivative of the present invention were lyophilized under the conditions where glycine and glucose were used as a stabilizer and shelved for 10 days. Then the values of anticomplement activity of thus lyophilized IgM were determined. The result is shown in Table 3 from which it is found that IgM derivatives of the present invention have an extremely high stability even after they are lyophilized. The IgM derivative used in the above test is an acetylated IgM in which R is a methyl group.

TABLE 3

| Immunoglobulin | Acylation percentage | Protein concentration | Anticomplement value before lyophilization | Anticomplement value after lyophilization |
|---|---|---|---|---|
| Acetylated IgM (I) | 3–8% | 2% | 29.0% | 29.5% |
| Acetylated IgM (II) | 20–25% | 2% | 3.2% | 3.6% |
| Intact IgM | 0 | 2% | Higher than 100% | Higher than 100% |

(4) Acute toxicity of IgM derivatives

Acute toxicity of a solution of IgM derivative of the present invention was tested with the use of mice. 0.25 µl each of a solution of IgM derivative and intact IgM (in both cases the protein concentration was 2%) was injected into the caudal vein of the mice and their conditions after the injection were observed. The result is shown in Table 4, from which it is understood that the acylation of IgM enhances the safety of IgM from the viewpoint of acute toxicity tested with the use of mice. The IgM derivative used in the above test is acetylated IgM.

TABLE 4

| Immunoglobulin | Acylation percentage | Protein concentration | Mortality | Temporaly debility | No change |
|---|---|---|---|---|---|
| Intact IgM | 0 | 2% | 2 | 7 | 1 |
| Acetylated IgM (I) | 3–8% | 2% | 0 | 2 | 8 |
| Acetylated IgM (II) | 20–25% | 2% | 0 | 2 | 8 |

Since IgM derivatives of the present invention maintain varied antibody activities while their anticomplement activity is decreased as mentioned above, they can be used for making immunoglobulin preparations for intravenous injection having no specific side effects. The immunoglobulin preparations for intravenous injection use of the present invention contain 20% or more by weight of acylated IgM derivatives prepared according to the aforementioned method. Since the content of IgM derivatives in excess of 20% by weight is enough for IgM preparations to display their pharmacological efficacy; the remaining 80% or less by weight of the ingredient may consist of any immunoglobulin other than IgM (for instance, IgG, IgA, etc.) and acylated IgG may also be contained partially as the case may require. Such immunoglobulin preparations for intravenous injection use can be manufactured according to the publicly known method of making IgG preparations for intra venous injection use.

For further clarity of disclosure of the present invention, the following examples are provided. % in the examples indicates % by weight.

EXAMPLE 1

A solution of 5% IgM was obtained by dialyzing the IgM fraction of 90% or more purity collected by the chromatographic method against an aqueous solution of 25% saturated sodium acetate. Acetic anhydride equivalent in weight to 6% of the whole immunoglobulin containing IgM was gradually added dropwise to 10 ml of the aqueous solution of 5% IgM with stirring while cooling with water and the reaction was carried on for another 1 hour with stirring while cooling with ice water likewise. Then the reaction solution was thoroughly dialyzed against a normal saline solution buffered with phosphate containing 0.2% polyethylene glycol-4000. 1.5% by weight of glycine and 1.0% by weight of glucose were added to the resulting solution of IgM derivative (acylation percentage: 20%) and the mixture was subjected to germ-free filtration and lyophilization to obtain the final preparation.

The anticomplement value CH 50 of a 1% solution of thus obtained preparation was 5%. The anticomplement value CH 50 of the IgM fraction of more than 90% purity exceeded 100%. The result of the investigation made on the agglutination this preparation with the use of E. coli NIHJJC-2, staphylococcus aureus 209P, and pseudomonas aeruginosa IFO 3080 made it clear that the preparation maintained the almost same agglutinationing activity as IgM fraction from which the preparation was made.

EXAMPLE 2

10 ml of a solution of 5% IgM obtained according to Example 1 was cooled to 0° to 5° C. and its pH was then adjusted to 8.0 with 1 N NaOH. Acetic anhydride equivalent in weight to 10% of the whole immunoglobulin containing IgM was gradually added thereto dropwise. During this process, the pH value of the reaction system was found turning to acid and was made slightly alkaline by adding an appropriate amount of 1 N NaOH. After the addition of acetic anhydride is completed, the reaction was continued for another 1 hour with stirring and the reaction solution was treated according to Example 1 to obtain the final product (acylation percentage: 38%). The anticomplement value CH50 of a 1% solution of this product was 4%, while the anticomplement value CH50 of IgM fraction before treatment was more than 100%. It was also found that the product maintained the same agglutination value as IgM from which it was made.

EXAMPLE 3

The final preparation was obtained according to Example 1, wherein succinic anhydride was used as an acylating agent instead of acetic anhydride.

The acylation percentage of this preparation was 25%, and the anticomplement value of its 1% solution was 10%. The preparation also maintained the same agglutination value as its material IgM.

EXAMPLE 4

The final preparation was obtained according to Example 1, wherein maleic anhydride was used as an acylating agent instead of acetic anhydride. Its acylation percentage was 20% and the anticomplement value of its 1% solution was 12%. It also maintained the same agglutination value as its material IgM.

EXAMPLE 5

The final preparation was obtained according to Example 1, wherein propionic anhydride was used as an acylating agent in the place of acetic anhydride. Its acylation percentage was 18% and the anticomplement value of its 1% solution was 11%. It also maintained the same agglutination value was its material IgM.

What is claimed is:

1. IgM derivatives into which acyl groups expressed by the following formula (I) are introduced to make their anticomplement activity weak by acylating the free amino groups existing in IgM up to 1–30% (acylation percentage)

$$-COR \quad (I)$$

where R indicates an alkyl group having 1 to 4 carbon atoms, or a carboxylated alkyl group expressed by —(CH$_2$)mCOOH (m is 2 or 3) or —CH=CHCOOH.

2. IgM derivatives according to claim 1, wherein the anticomplement value of a solution of 1% IgM derivative is 50% or less.

3. A process for the preparation of I$_g$M derivatives whose anticomplement activity is weakened comprising acylating 1 to 30% (acylation percentage) of the free amino groups existing in I$_g$M with an acylating agent in an amount of 0.5 to 20% based on the weight of the I$_g$M which contains acyl groups expressed by the following formula (I) in their molecules $$-COR \quad (I)$$

where R indicates an alkyl group having 1 to 4 carbon atoms, or a carboxylated alkyl group expressed by —(CH$_2$)mCOOH (m is 2 or 3) or —CH=CHCOOH.

4. An immunoglobulin preparation for intravenous injection use which contains 20% by weight or more of I$_g$M derivatives into which acyl groups expressed by the following formula (I) are introduced to make their anticomplement activity weak by acylating the free amino groups existing in I$_g$M up to 1–90% (acylation percentage)

$$-COR \quad (I)$$

where R indicates an alkyl group having 2 to 4 carbon atoms, or a carboxylated alkyl group expressed by —(CH$_2$)mCOOH (m is 2 or 3) or —CH=CHCOOH, wherein the balance composition comprises serum proteins or derivatives thereof other than I$_g$M.

5. A process as in claim 3, wherein the acylating agent is selected from the group consisting of acetic acid, propionic acid, butyric acid, valeric acid, succinic acid, glutaric acid, maleic acid, or an anhydride, acid chloride or ester thereof.

6. The process of claim 3, wherein said acylating is conducted in water.

7. The process of claim 6, wherein said acylating is at a pH of 6 to 10, at a temperature of 50° C. or lower and for a time of 5 minutes to 5 hours.

8. The process of claim 7, wherein said acylating is conducted with stirring which does not cause denaturation of globulin.

9. The process of claim 8, wherein after acylating is completed the I$_g$M derivative is obtained by dialyzing the reaction mixture against water.

10. A preparation as claimed in claim 4, wherein the acylation percentage is 1 to 30%.

* * * * *